US010182939B2

(12) United States Patent
Canelli et al.

(10) Patent No.: US 10,182,939 B2
(45) Date of Patent: Jan. 22, 2019

(54) HYDRAULIC INJECTOR AND METHODS FOR INTRA-OCULAR LENS INSERTION

(71) Applicant: Novartis AG, Basel (CH)

(72) Inventors: Hugh B. Canelli, Burleson, TX (US);
Partha Chandrakant, Irvine, CA (US);
James Y. Chon, Irvine, CA (US); Gary P. Sorensen, Mission Viejo, CA (US);
Daniel J. Wilson, Lake Forest, CA (US); Raphael Gordon, Ladera Ranch, CA (US)

(73) Assignee: Novartis AG, Basel (CH)

( * ) Notice: Subject to any disclaimer, the term of this patent is extended or adjusted under 35 U.S.C. 154(b) by 489 days.

(21) Appl. No.: 14/855,855

(22) Filed: Sep. 16, 2015

(65) Prior Publication Data

US 2017/0071787 A1 Mar. 16, 2017

(51) Int. Cl.
*A61F 2/16* (2006.01)
*A61F 9/007* (2006.01)
*A61F 9/00* (2006.01)

(52) U.S. Cl.
CPC ........ *A61F 9/00736* (2013.01); *A61F 2/1662* (2013.01); *A61F 9/0017* (2013.01); *A61F 9/0008* (2013.01)

(58) Field of Classification Search
CPC ... A61F 9/00736; A61F 2/1662; A61F 9/0017
USPC ................................ 606/107; 623/6.11, 6.12
See application file for complete search history.

(56) References Cited

U.S. PATENT DOCUMENTS

| 3,089,815 A | 5/1963 | Lieb et al. |
| 3,301,190 A | 1/1967 | Gondek |
| 3,608,549 A | 9/1971 | Merrill |
| 3,982,537 A | 9/1976 | Bucalo |
| 4,007,742 A | 2/1977 | Banko |
| 4,030,499 A | 6/1977 | Bucalo |
| 4,054,138 A | 10/1977 | Bucalo |
| 4,122,850 A | 10/1978 | Bucalo |
| 4,184,510 A | 1/1980 | Murry et al. |
| 4,246,932 A | 1/1981 | Raines |

(Continued)

FOREIGN PATENT DOCUMENTS

| EP | 0348146 | 12/1989 |
| GB | 1551767 | 8/1979 |

(Continued)

OTHER PUBLICATIONS

International Searching Authority, International Preliminary Report on Patentability, PCT/US2008/067590, dated Jan. 19, 2010, 8 pages.

(Continued)

*Primary Examiner* — Vy Bui

(57) ABSTRACT

A hydraulically-driven Intra-Ocular Lens (IOL) insertion tool includes a body, a chamber within the body, a first fluid port providing fluid communication into the chamber, a piston positioned within the chamber and arranged to move within the chamber in response to the introduction or removal of fluid from the chamber, and an elongated member. The elongated member includes a distal end comprising an intra-ocular lens interface and a proximal end connected to the piston such that movement of the piston within the chamber causes corresponding movement of the elongated member.

15 Claims, 5 Drawing Sheets

(56) References Cited

U.S. PATENT DOCUMENTS

| | | |
|---|---|---|
| 4,265,618 A | 5/1981 | Herskovitz et al. |
| 4,357,136 A | 11/1982 | Herskovitz et al. |
| 4,392,827 A | 7/1983 | Martin |
| 4,474,752 A | 10/1984 | Haslam et al. |
| 4,484,915 A | 11/1984 | Tartaglia |
| 4,582,488 A | 4/1986 | Newman |
| 4,684,344 A | 8/1987 | Brockway et al. |
| 4,704,088 A | 11/1987 | Newman |
| 4,713,446 A | 12/1987 | Devore et al. |
| 4,795,423 A | 1/1989 | Osterholm |
| 4,830,855 A | 5/1989 | Stewart |
| 4,862,885 A | 9/1989 | Cumming |
| 4,992,045 A | 2/1991 | Beisel |
| 5,066,276 A | 11/1991 | Wang |
| 5,066,297 A | 11/1991 | Cumming |
| 5,095,914 A | 3/1992 | Sarstedt |
| 5,120,307 A | 6/1992 | Wang |
| 5,176,502 A | 1/1993 | Sanderson et al. |
| 5,328,481 A | 7/1994 | Wang |
| 5,336,175 A | 8/1994 | Mames |
| 5,360,413 A | 11/1994 | Leason et al. |
| 5,370,630 A | 12/1994 | Smidebush et al. |
| 5,476,511 A | 12/1995 | Gwon et al. |
| 5,487,725 A | 1/1996 | Peyman |
| 5,582,595 A | 12/1996 | Haber et al. |
| 5,620,700 A | 4/1997 | Berggren et al. |
| 5,728,102 A | 3/1998 | Feingold et al. |
| 5,743,886 A | 4/1998 | Lynn et al. |
| 5,773,019 A | 6/1998 | Ashton et al. |
| 5,783,205 A | 7/1998 | Berggren et al. |
| 5,824,072 A | 10/1998 | Wong |
| 5,860,949 A | 1/1999 | Chen |
| 5,928,663 A | 7/1999 | Peyman |
| 5,984,889 A | 11/1999 | Christ et al. |
| 6,210,357 B1 | 4/2001 | Morris |
| 6,270,343 B1 | 8/2001 | Martin |
| 6,290,690 B1 | 9/2001 | Huculak et al. |
| 6,372,246 B1 | 4/2002 | Wei et al. |
| 6,413,245 B1 | 7/2002 | Yaacobi et al. |
| 6,419,656 B1 | 7/2002 | Vetter et al. |
| 6,436,143 B1 | 8/2002 | Ross et al. |
| 6,488,659 B1 | 12/2002 | Rosenman |
| 6,585,700 B1 | 7/2003 | Trocki et al. |
| 6,635,267 B1 | 10/2003 | Miyoshi et al. |
| 6,645,179 B1 | 11/2003 | Ishikawa et al. |
| 6,726,654 B2 | 4/2004 | Rosenman |
| 6,991,457 B2 | 1/2006 | Kazen et al. |
| 7,316,676 B2 | 1/2008 | Peyman et al. |
| 7,364,570 B2 | 4/2008 | Gerondale et al. |
| 8,096,972 B2 | 1/2012 | Varner et al. |
| 8,617,106 B2* | 12/2013 | Zacharias ............ A61M 1/0031 604/119 |
| 8,758,433 B2* | 6/2014 | Cole ..................... A61F 2/1662 623/6.12 |
| 2004/0052761 A1 | 3/2004 | Vernon et al. |
| 2004/0176720 A1 | 9/2004 | Kipfer |
| 2005/0177137 A1 | 8/2005 | Kipfer |
| 2006/0047250 A1 | 3/2006 | Hickingbotham et al. |
| 2007/0038174 A1 | 2/2007 | Hopkins |
| 2007/0060887 A1 | 3/2007 | Marsh et al. |
| 2007/0270750 A1 | 11/2007 | Dacquay et al. |
| 2009/0018512 A1 | 1/2009 | Charles |
| 2011/0264102 A1 | 10/2011 | Cole et al. |
| 2014/0323953 A1 | 10/2014 | Sorensen et al. |
| 2015/0342726 A1* | 12/2015 | Deacon ................... A61F 2/148 623/6.12 |

FOREIGN PATENT DOCUMENTS

| | | |
|---|---|---|
| WO | 8203761 | 11/1982 |
| WO | 8700029 | 1/1987 |
| WO | 9603978 | 2/1996 |
| WO | 9933853 | 7/1999 |
| WO | 0110482 | 2/2001 |
| WO | 0139701 | 6/2001 |
| WO | 03094992 | 11/2003 |
| WO | 2006050008 | 5/2006 |
| WO | 2014089250 A1 | 6/2014 |

OTHER PUBLICATIONS

International Searching Authority, International Search Report, PCT/US2008/067590, dated Oct. 2, 2008, 3 pages.

International Searching Authority, Written Opinion, PCT/US2008/067590, dated Oct. 2, 2008, 7 pages.

Parker: Your Resource for Motion and Fluid Control Components, Systems and Solutions—System Solutions for Life Sciences; 2003; Aurora Instruments, LLC Brochure; 8 pages.

Ultra™ 2800 Positive Displacement Dispenser; 2004; EFD, Inc. Brochure XP 1104 vol. 11.10; 2 pages.

International Searching Authority, International Search Report and Written Opinion, PCT/IB2016/053569, dated Aug. 12, 2016, 21 pages.

* cited by examiner

HYDRAULIC INJECTOR AND METHODS FOR INTRA-OCULAR LENS INSERTION

TECHNICAL FIELD

The present disclosure is directed to methods and systems for performing ophthalmic surgical procedures, and more particularly, to methods and systems for treating a patient by inserting an intra-ocular lens into the patient's eye.

BACKGROUND

The human eye, in simple terms, functions to provide vision by transmitting and refracting light through a clear outer portion called the cornea and focusing the light by way of the lens onto the retina at the back of the eye. The quality of the visual image created by the focused light depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the natural lens and implantation of an artificial lens, typically termed an Intra-ocular Lens (IOL).

An IOL insertion cartridge may be used to fold and insert an IOL through a relatively small incision into the eye. The IOL insertion cartridge may fold the IOL as it advances therethrough. A plunger-like device, manually pressed by a user, such as a surgeon, advances the lens through the IOL insertion cartridge. However, as the lens advances, the forces that the physician exerts on the plunger to advance the lens can drastically and suddenly decrease, causing the IOL to suddenly shoot into the eye. This can cause improper IOL placement and may cause damage to eye tissue.

SUMMARY

According to one example, a hydraulically-driven Intra-Ocular Lens (IOL) insertion tool includes a body, a chamber within the body, a first fluid port providing fluid communication into the chamber, a piston positioned within the chamber and arranged to move within the chamber in response to the introduction or removal of fluid from the chamber, and an elongated member. The elongated member includes a distal end comprising an intra-ocular lens interface and a proximal end connected to the piston such that movement of the piston within the chamber causes corresponding movement of the elongated member.

According to one example, a system for Intra-Ocular Lens (IOL) insertion includes a surgical console that includes a fluid source and an aspiration pump. The system further includes a hydraulically-driven IOL insertion tool having a chamber, a first fluid port in fluid connection with the chamber, and a second fluid port in fluid connection with the chamber, a piston in connection with an elongated member, the elongated member having a distal end comprising an intra-ocular lens interface, a first fluid line providing fluid communication between the fluid source and the first fluid port, and a second fluid line providing fluid communication between the aspiration pump and the second fluid port.

According to one example, a method for inserting an Intra-Ocular Lens (IOL) includes connecting a hydraulically-driven IOL insertion hand-piece to a fluid source, the hand-piece comprising a chamber and a piston in connection with an IOL interface. The method further includes priming a hydraulic chamber of the hand-piece, engaging the hand-piece with an IOL insertion cartridge, and hydraulically actuating the piston to move the IOL interface in a distal direction with respect to the IOL lens cartridge.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
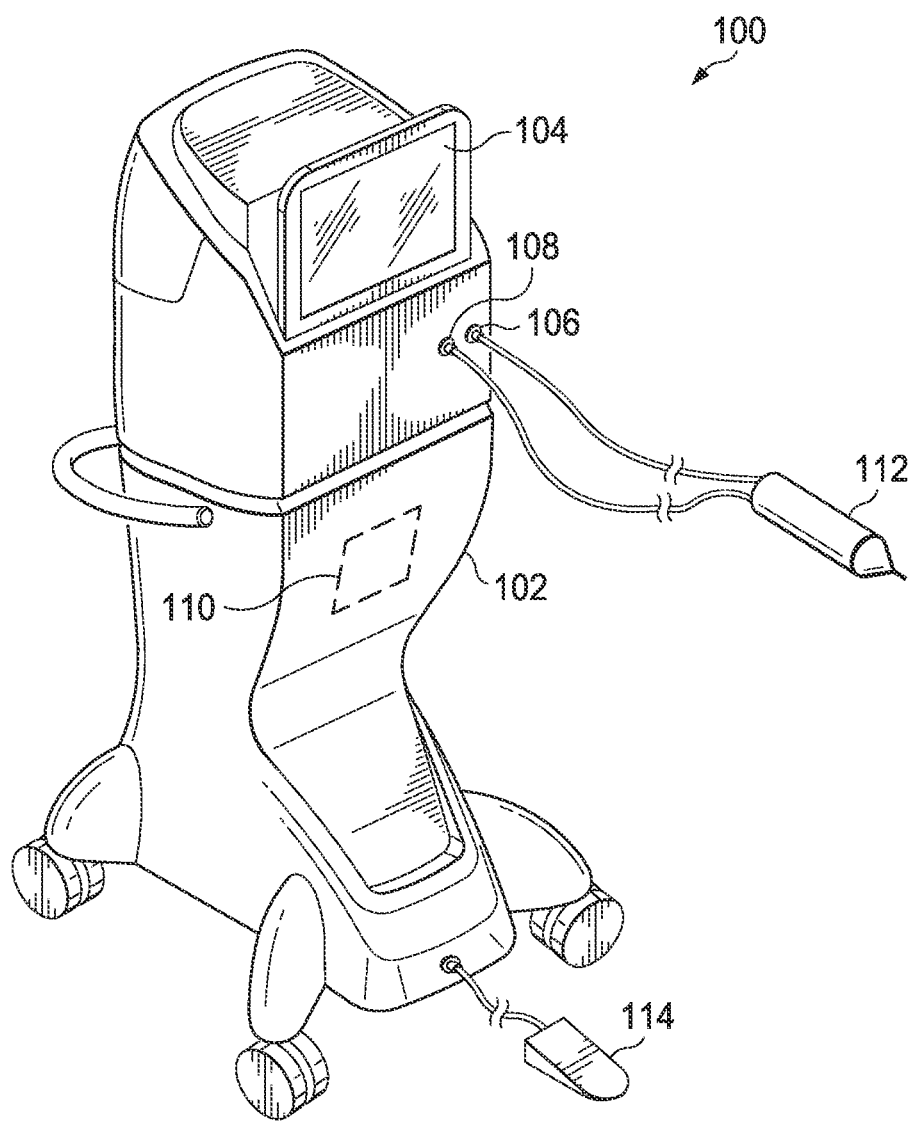
FIG. 1 is a diagram showing an illustrative ophthalmic surgical system.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

As described above, as the IOL is inserted, the forces exerted on the plunger to move the lens can drastically and suddenly decrease, causing the IOL to suddenly shoot into the eye, causing improper IOL placement and damage to eye tissue. This disclosure is directed to a hydraulically-driven IOL insertion tool that may provide consistent IOL advancement despite the change or decrease resistance.

In some implementations, the fluids used to hydraulically drive the IOL insertion tool may be the same fluids used during other processes of cataract surgical procedures. For example, cataract replacement procedures may employ a phacoemulsification tool that uses ultrasonic energy to break up or emulsify an existing natural lens. The emulsified lens tissue may then be aspirated by an aspiration tool in communication with an aspiration pump. In addition, an irrigation tool may replace aspirated eye fluid with fluid from a fluid. As described herein, some embodiments use the aspiration pump and the fluid source to drive the hydraulically-driven IOL insertion tool.

In one example described herein, the IOL insertion tool includes a body, a chamber within the body, and a fluid port providing fluid communication into the chamber. Fluid pumped into and out of the chamber through the fluid port drives a piston. In this example, the piston is secured to a proximal end of an elongated member that has an IOL interface at its distal end. Fluid may be pumped into the chamber to advance the IOL interface forward through the IOL cartridge in a controlled manner. In some embodiments, the fluid is pumped using a foot pedal.

An IOL insertion tool embodying principles described herein may provide a number of advantages not found in conventional IOL insertions tools. For example, an IOL insertion tool actuated by hydraulics advances the IOL with a smooth, consistent forward motion that may be difficult to achieve with manual insertion systems. In some implementations, the IOL insertion tool is a hand-piece controlled by a foot-pedal so that an operator can hold the hand-piece with both hands while controlling the insertion of the IOL by foot. In one example, the IOL insertion tool hand-piece may be a low-cost single-use hand-piece.

FIG. 1 is a diagram showing an illustrative ophthalmic surgical system 100. According to the present example, the ophthalmic surgical system 100 includes a surgical console 102 and a hydraulically-driven IOL insertion tool 112. The surgical console 102 may include a display screen 104, an irrigation port 106, an aspiration port 108, and an input mechanism 114. In this example, the input mechanism 114 is a foot pedal. However, other input mechanisms may also be used, such as switches, buttons, triggers, touchscreen elements, keyboards, mice, and others. In one implementation, the surgical console 102 is designed to be mobile and may be used by a user, such as a health care provider, to perform ophthalmic surgical procedures. The surgical console 102 may also include a control system 110 that may be configured to process, receive, and store data to perform various functions associated with the IOL insertion tool 112.

The display screen 104 may communicate information to the user, and in some implementations, may show data relating to system operation and performance during a surgical procedure. In some examples, the display screen 104 is a touchscreen that allows the operator to interact with the surgical console 102 through a graphical user interface.

The surgical console 102 may include various fluid handling systems for use during various ophthalmic surgical procedures. In this example, the surgical console 102 may provide irrigation fluid through the irrigation port 106. The surgical console 102 may include a pump that can create a vacuum or suction force that may aspirate fluid and tissue through the aspiration port 108. In one implementation, the hydraulically-driven IOL insertion tool 112 may use these or other fluid handling systems to drive the hydraulically-driven IOL insertion tool 112. Specifically, the hydraulically-driven IOL insertion tool 112 may be connected to the irrigation port 106 through an irrigation line and may be connected to the aspiration port 108 through an aspiration line.

Figure 2:
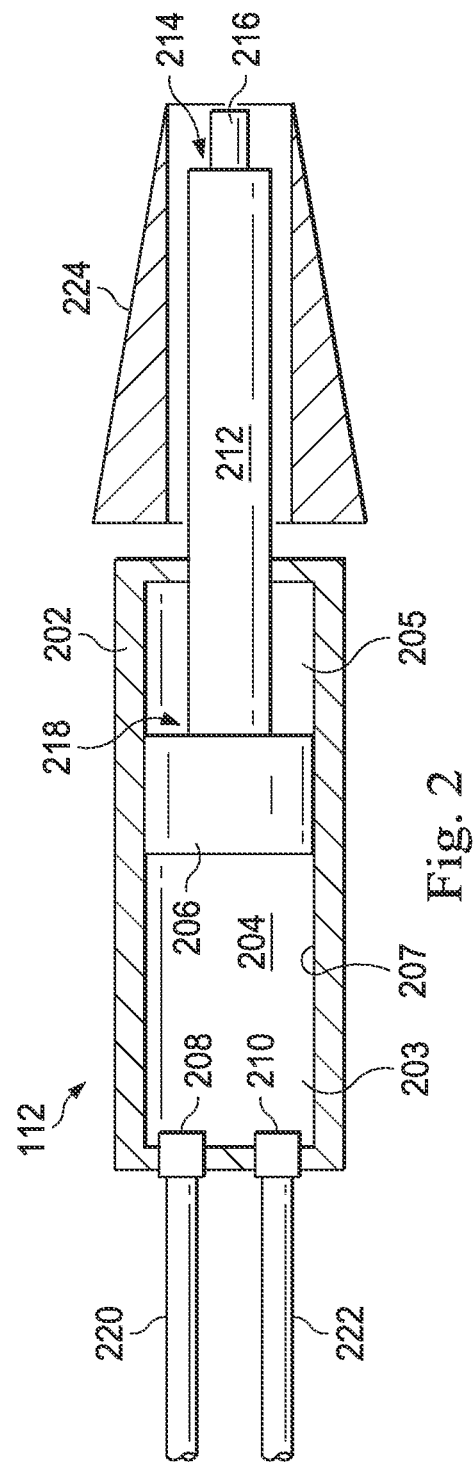
FIG. 2 is a schematic diagram of an illustrative hydraulically-driven IOL insertion tool.

FIG. 2 is a schematic diagram of the illustrative hydraulically-driven IOL insertion tool 112, which may be referred to as a hand-piece. According to the present example, the hydraulically-driven IOL insertion tool 112 includes a body 202 having a hydraulic chamber 204 disposed within. Positioned within the hydraulic chamber 204 is a piston 206. The piston 206 is secured to an elongated member 212 that extends outside the hydraulic chamber 204. The proximal end 218 of the elongated member 212 is secured to the piston 206 and the distal end 214 of the elongated member 212 includes an IOL interface 216. Thus, movement of the piston 206 causes corresponding movement of the IOL interface 216. Movement of the piston 206 is effected by pumping a fluid into the hydraulic chamber 204. As will be described in further detail below, fluid may be pumped in through an irrigation line 220 connected to the hydraulic chamber 204 through a first fluid port 208 and/or an aspiration line 222 connected to the hydraulic chamber 204 through a second fluid port 210.

The body 202 of the hand-piece may be made of a rigid material. The body 202 may be shaped for easy grasping by an operator. For example, the body 202 may include a gripping feature (not shown) on the outer surface of the body 202. The body 202 may be hollow and include a number of features therein, such as the hydraulic chamber 204. In one example, the hydraulic chamber 204 may be formed by the inner surface 207 of the body 202. In some examples, however, the hydraulic chamber 204 may be formed by a separate element, such as a hollow cylindrical body (not shown), that is supported and housed within the body 202.

The piston 206 engages the inner surface 207 that forms the hydraulic chamber 204 such that it divides a proximal portion 203 of the hydraulic chamber 204 from a distal portion 205 of the hydraulic chamber 204. The piston 206 may form a seal with the inner surface 207 such that it prevents fluid from flowing between the distal portion 205 and the proximal portion 203. The shape of the piston 206 may match the shape of the hydraulic chamber 204. For example, if the hydraulic chamber 204 is substantially cylindrical, then the piston 206 may be substantially circular when viewed from an axial direction of the hydraulic chamber 204. In some examples, the proximal portion 205 may be in fluid communication with an environment external to the body 202. For example, the body 202 may have one or more through-holes that allow air to flow in and out of the distal portion 205 as the piston 206 moves in either a distal or proximal direction.

In one implementation, the piston 206 may be secured to the elongated member 212. In the present example, the elongated member 212 is directly connected to the piston 206. In some examples, however, connector elements may be positioned between the piston 206 and the elongated member 212 to provide the desired connection. In any case, movement of the piston 206 within the hydraulic chamber 204 causes corresponding movement of the elongated member 212. Specifically, as the piston 206 moves in a distal direction, the elongated member 212 moves in the distal direction. As the piston 206 moves in a proximal direction, the elongated member 212 moves in the proximal direction.

The elongated member 212 includes an IOL interface 216 at the distal end 214 of the elongated member 212. The IOL interface 216 is designed to hold an IOL (not shown) that is to be inserted into a patient's eye. The elongated member 212 is sized and shaped to fit within an IOL insertion cartridge 224. In some implementations, the IOL insertion cartridge 224 is selectively attachable to the body 202. In other implementations, the IOL insertion cartridge 224 is fixed to the body 202. The IOL insertion cartridge 224 may be arranged to house an IOL for injection into a surgical site. In some implementations, the IOL insertion cartridge 224 includes a number of structural features that fold the IOL as it advances so that it can be passed into the eye of the patient.

In the present example, the proximal portion 203 of the hydraulic chamber 204 includes a first fluid port 208 and a second fluid port 210. The first fluid port 208 is connected to a first fluid line, which will be referred to as an irrigation line 220. The irrigation line 220 is in fluid communication with a fluid source (not shown) and is arranged to provide fluid communication between the fluid source and the hydraulic chamber 204. The second fluid port 210 is connected to a second fluid line, which will be referred to as an aspiration line 222. Depending on the implementation, the aspiration line 222 may be in fluid communication with an aspiration pump, as will be described in further detail below. Fluid from the irrigation line 220 and/or aspiration line 222 is pumped into the proximal portion 203 of the hydraulic chamber 204, thereby moving the piston 206, elongated member 212, and IOL interface 216 in a distal direction. Additionally, fluid is pumped out of the proximal portion 203 of the hydraulic chamber 204 to move the piston 206, elongated member 212, and IOL interface 216 in a proximal direction.

In one implementation, the first fluid port 208 includes a check valve (not shown) that allows fluid to flow into the hydraulic chamber 204 while preventing fluid from flowing out of the hydraulic chamber 204 through the first fluid port 208. Thus, fluid that is pumped into the hydraulic chamber either through the first fluid port 208 or the second fluid port 210 cannot leak backwards into the irrigation line 220.

Figure 3:
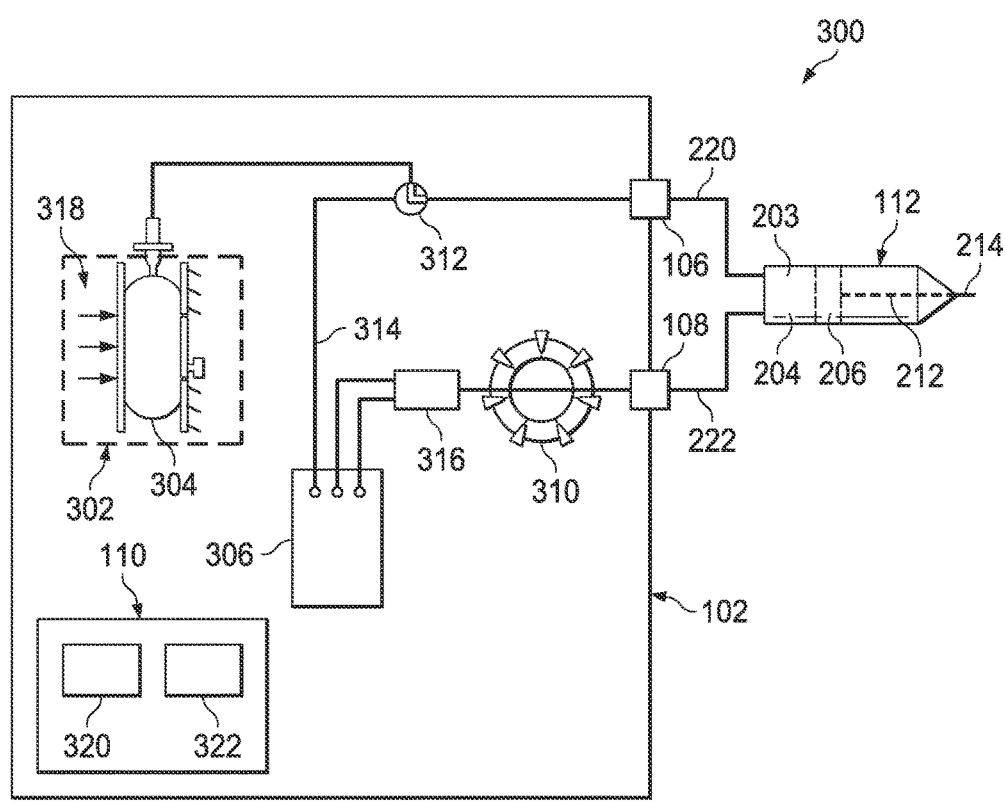
FIG. 3 is a schematic diagram of a surgical console and the hydraulically-driven IOL insertion tool.

FIG. 3 is a schematic diagram of an IOL insertion system 300 that includes the surgical console 102 and the hydraulically-driven IOL insertion tool 112. According to the present example, the surgical console 102 includes a fluid source 302 and an aspiration pump 310. As described above, such components may be used for other aspects of cataract replacement procedures besides IOL insertion. According to principles described herein, the IOL insertion tool 112 may be designed to use the aspiration pump 310 and fluid source 302 that are typically used for phacoemulsification procedures to hydraulically power the IOL insertion tool 200.

The irrigation line 220 connects the hydraulically-driven IOL insertion tool 112 to the surgical console 102 through the irrigation port 106 to provide irrigation fluid to the hydraulically-driven IOL insertion tool 112. The irrigation port 106 is in fluid communication with the fluid source 302 through a switch valve 312. The switch valve 312 may be used to selectively direct fluid from the fluid source 302 to either the irrigation port 106 or through a shunt line 314 to a drain chamber 306 such as a drain bag. The switch valve 312 may also be in an off position and not allow any fluid to pass from the fluid source 302. For example, when a surgical device, such as the hydraulically-driven IOL insertion tool 112 or other instrument, is connected to the irrigation port 106 but does not currently need irrigation fluid, then the switch valve 312 may be positioned in the off position. When the device connected to the irrigation port 106 desires to use the fluid from the fluid source 302, the switch valve 312 is positioned to direct fluid to the irrigation port 106 and into the irrigation line 220. To drain the fluid source, which may be done after a surgical procedure, for example, the switch valve 312 can be set to direct fluid through the shunt line 314 into the drain chamber 306.

In the present example, the fluid source 302 includes a fluid bag 304. The fluid bag 304 is compressed by a compression mechanism 318 that forces the fluid within the fluid bag 304 into the irrigation line 220. In one example, the fluid is a saline fluid that is safe for injection into a patient's eye. However, other fluids also may be used.

The aspiration line 222 connects the hydraulically-driven IOL insertion tool 112 to the surgical console 102 through the aspiration port 108 to pump fluid into and out of the hydraulically-driven IOL insertion tool 112. The aspiration port 108 is in fluid communication with an aspiration pump 310. The aspiration pump 310 pumps fluid from the aspiration line 222 and deposits such fluid into a reservoir 316. Fluid in the reservoir 316 is moved into the drain chamber 306. In some examples, the aspiration pump 310 is configured to be put into reverse and pump fluid back through the aspiration line 222. The use for such a configuration will be described in further detail below. The aspiration pump 310 may be one of a variety of pumps, including an elastomeric pump and a peristaltic pump. Other types of pumps are contemplated as well.

As previously indicated, the surgical console 102 includes the control system 110. The control system 110 may include one or more processors 320 and one or more memory elements 322. The memory element 322 may include various types of memory including volatile memory (such as Random Access Memory (RAM)) and non-volatile memory (such as solid state storage). The memory element 322 may store computer readable instructions, that when executed by the processor 320, cause the control system 110 to perform various functions, including managing the fluid source 302, switch valve 312, and aspiration pump 310.

The control system 110 may manage the components of the surgical console 102 to perform various operations associated with the hydraulically-driven IOL insertion tool 112. Such operations include, among others, a priming operation, a distal-direction actuation operation, and a proximal-direction actuation operation. When a user desires to use the hydraulically-driven IOL insertion tool 112, the user connects the tool to the irrigation line 220 and the aspiration line 222. The user may then instruct the surgical console 102 to begin the priming operation.

The priming operation prepares the IOL insertion tool 112 for use. Specifically, when the IOL insertion tool 200 is first connected to the irrigation line 220 and aspiration line 222, there may still be air in the proximal portion 203 of the hydraulic chamber 204. During the priming operation, the control system 110 causes the fluid source 302 to inject fluid into the irrigation line 220 and into the hydraulic chamber 204. The irrigation fluid is pumped into the hydraulic chamber 204 through the first fluid port (e.g., 208, FIG. 2), which, as described above, may include a check valve. Thus, the irrigation fluid does not flow back through the irrigation line 220. For the priming operation, the control system 110 also causes the aspiration pump 310 to operate in a forward manner. In other words, the aspiration pump 310 pumps air out of the aspiration line 222. This creates a vacuum that is then filled by fluid being pumped into the hydraulic chamber 204 through the irrigation line 220. After the fluid fills the irrigation line 220, the hydraulic chamber 204, and the aspiration line 222, the priming process is complete.

In one example, to actuate the piston 206 of the hydraulically-driven IOL insertion tool 112 in a distal direction, the control system 110 causes the fluid source 302 to inject fluid into the irrigation line 220, and thus applies pressure to the fluid within the hydraulic chamber 204 of the hydraulically-driven IOL insertion tool 112. In some examples, in addition to pressure provided by the fluid source 302, the control system 110 causes the aspiration pump 310 to operate in reverse. The aspiration pump 310 thus pumps fluid that is within the aspiration line 222 back into the hydraulic chamber 204, thus providing additional pressure to move the piston 206 forward in the distal direction.

Forward (i.e., distal) motion of the piston 206 moves the elongated member 212 and the IOL interface 214 forward with respect to the IOL insertion cartridge (e.g., 224. FIG.

2). The user may control the forward movement of the IOL through an input mechanism such as a foot pedal. Other input mechanisms such as buttons, dials, touchscreen elements, and others are contemplated as well.

In one example, to actuate the piston 206 of the hydraulically-driven IOL insertion tool 112 in a proximal direction, the control system 110 causes the aspiration pump 310 to operate as usual and pump fluid out of the aspiration line 222. In addition, the control system 110 may set the switch valve 312 to an off position so that fluid does not flow into the irrigation line 220. As the aspiration pump 310 pumps fluid out of the aspiration line, a vacuum is created within the hydraulic chamber 204 of the hydraulically-driven IOL insertion tool 112. This vacuum then pulls the piston 206 in the proximal direction. Such backward motion of the piston 206 may be performed after the IOL has been put into place. Alternatively, the user may wish to cause backward motion of the piston 206 before the IOL has been put into place. For example, if the IOL did not fold properly while passing through the IOL insertion cartridge 224, then the user may wish to move the IOL backwards and re-insert the IOL through the IOL insertion cartridge 224.

Figure 4:
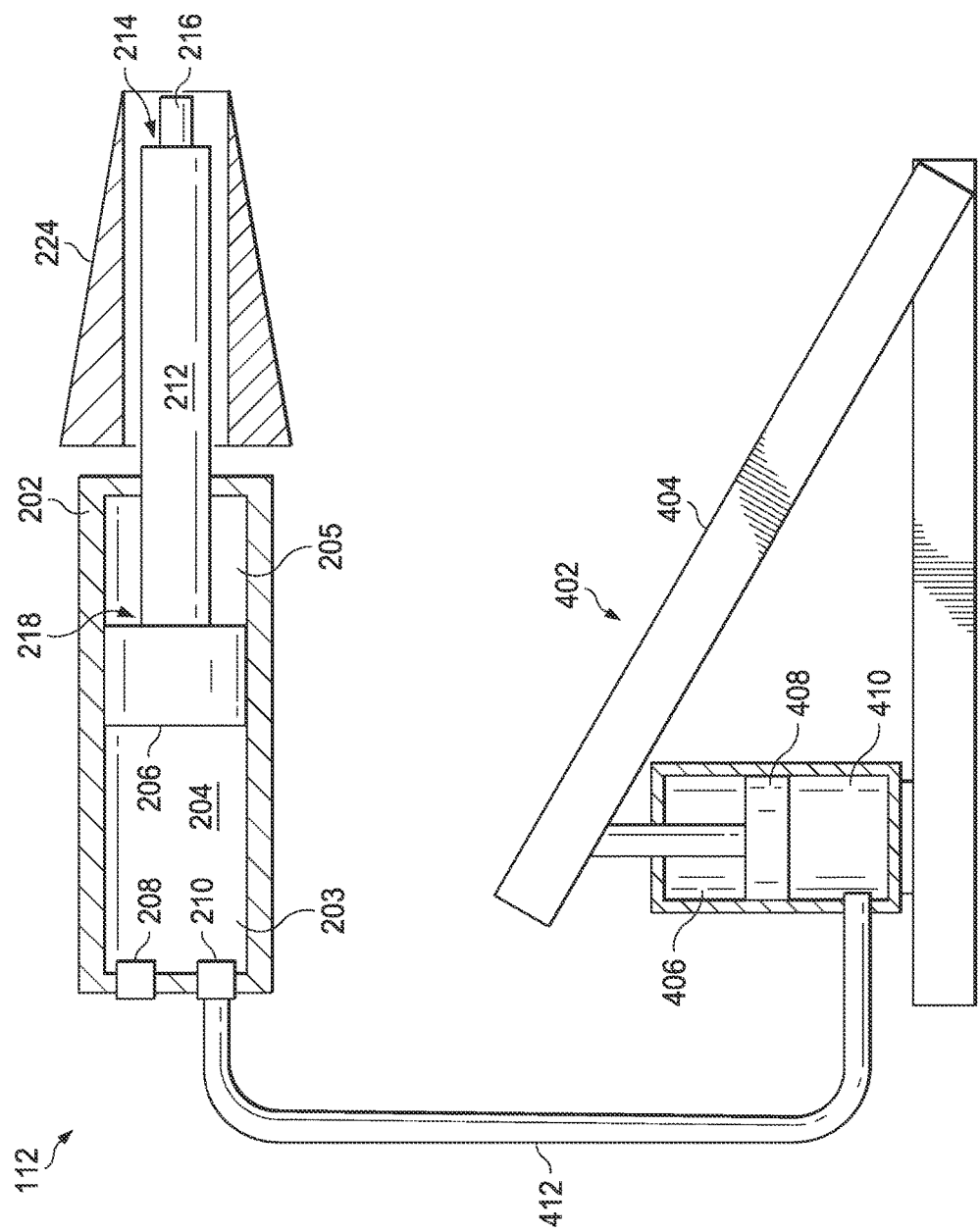
FIG. 4 is a diagram showing a foot pedal with a master chamber in connection with a slave chamber within the hydraulically-driven IOL insertion tool.

FIG. 4 is a diagram showing an illustrative foot pedal 402 used to drive the hydraulically-driven IOL insertion tool 112. Thus, in the present example, the hydraulically-driven IOL insertion tool 112 is powered by the foot pedal 402 instead of components of the surgical console (e.g., 102, FIG. 1). According to the present example, the second fluid port 210 is connected to a fluid line 412. The first fluid port 208 remains closed and unconnected to a fluid line. The fluid line 412 provides fluid communication between the hydraulic chamber 204 and a master chamber 406 within the foot pedal 402. In this example, the hydraulic chamber 204 acts as a slave chamber.

In the present example, the foot pedal 402 includes a hinged element 404 that is connected to a piston 408 within the master chamber 406. When a user steps on the hinged element 404 and presses it downward, the piston 408 is also pressed downward. This presses any fluid within the lower portion 410 of the master chamber 406 through the fluid line 412 and into the proximal portion 203 of the hydraulic chamber 204. This, in turn, applies pressure to the piston 206 to move the piston 206 in the distal direction.

In one example, the hinged element 404 is biased so that it moves back up when the user's foot is no longer pressing down on the hinged element 404. This pulls the piston 408 upwards and creates a vacuum in the lower portion 410 of the master chamber 406, thus drawing fluid from the proximal portion 203 of the hydraulic chamber 204. This creates a vacuum within the hydraulic chamber 204 that causes the piston 206 to move in the proximal direction.

In one example, to prime the hydraulically-driven IOL insertion tool 112 after it is first connected to the fluid line 412, the first fluid port 208 may be temporarily connected to a fluid source through the first fluid port 208. As described above, first fluid port 208 may include a one-way check valve that allows fluid to flow through the fluid port 208 into the hydraulic chamber 204 but does not allow fluid to pass outwardly through the fluid port 208 out of the hydraulic chamber 204. In one example, the fluid source may be the fluid source (e.g., 302, FIG. 3) described above. In such case, the first fluid port 208 may be connected to the irrigation port 106 of the surgical console through an irrigation line (e.g., 222, FIG. 2). In one example, a separate fluid source that is not associated with the surgical console 102 may be temporarily connected to the first fluid port 408 for the priming operation.

Figure 5:
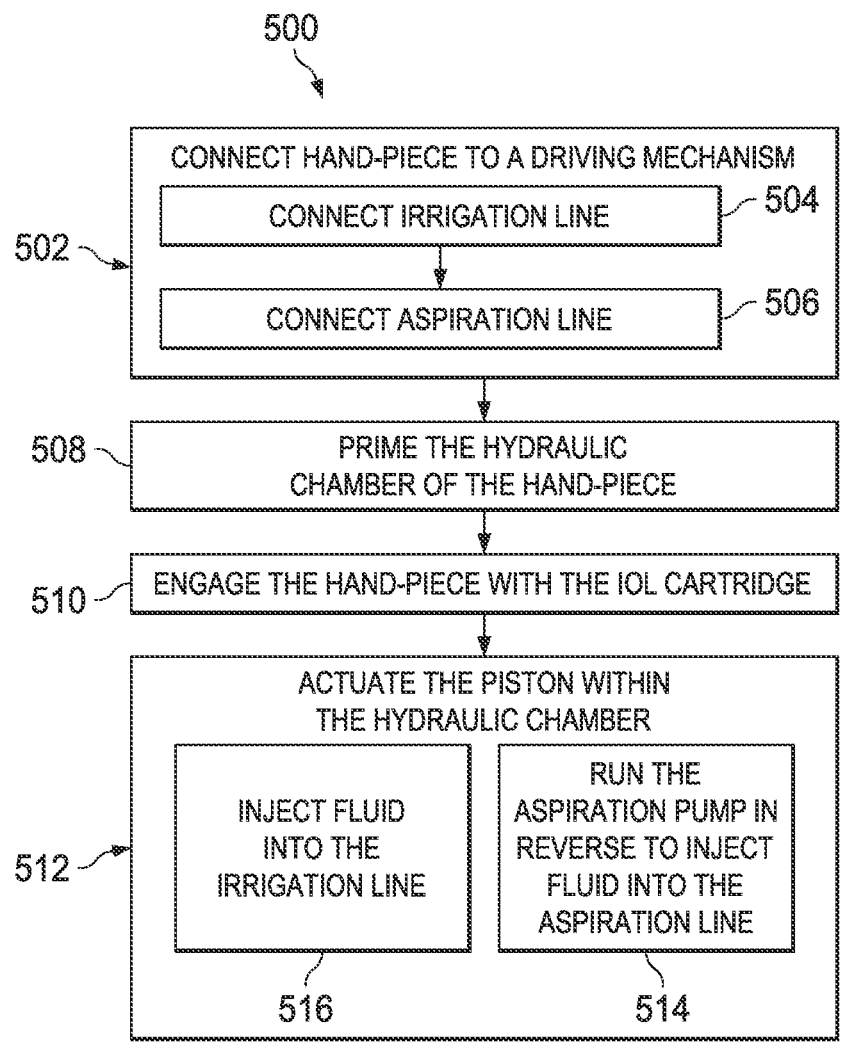
FIG. 5 is an example flowchart showing an illustrative method for using a hydraulically-driven IOL insertion tool to insert an IOL into a patient's eye.

FIG. 5 is an example flowchart showing an illustrative method 500 for using a hydraulically-driven IOL insertion tool to insert an IOL into a patient's eye. According to the present example, at step 502, a user connects the hand-piece (i.e., the hydraulically-driven IOL insertion tool) to a driving mechanism. To connect the hand-piece to the driving mechanism, the user connects the hand-piece to an irrigation line at step 504 and connects the hand-piece to an aspiration line at step 506.

In one example, the driving mechanism is the surgical console (e.g., 102, FIG. 1) described above. In such case, the irrigation line is in fluid communication with a fluid source within the surgical console 102 and the aspiration line is in fluid communication with an aspiration pump within the surgical console 102.

In another example, the driving mechanism is the foot pedal (e.g., 402, FIG. 4) described above. In such case, the irrigation line is a temporary connection and provides fluid communication with a fluid source. Such a fluid source may be within the surgical console 102 or may be a separate fluid source. The aspiration line is connected to a master chamber of the foot pedal 402.

At step 508, the hydraulic chamber of the hand-piece is primed. In some cases, this may be done manually by a user by connecting the hand-piece to a fluid source to fill the hydraulic chamber with fluid. In some cases, the control system (e.g., 110, FIG. 1) of the surgical console 102 may cause the fluid source to inject fluid into the hydraulic chamber. The hand-piece may be a single-use hand-piece and may come packaged without any fluid within the hydraulic chamber. Thus, the priming step provides the fluid to prepare the hydraulic chamber for hydraulic operations.

At step 510, the user engages the hand-piece with the IOL insertion cartridge. In some examples, the user also positions the IOL insertion cartridge with respect to the patient's eye so that when the IOL passes through the IOL insertion cartridge, the IOL is properly placed within the patient's eye.

At step 512, the user causes the piston to actuate within the hydraulic chamber to move the IOL forward and into place in the patient's eye. In the case where the hydraulically-driven IOL insertion tool uses driving mechanisms of the surgical console, the user may cause the piston to actuate through an input mechanism such as a foot pedal or button. Use of the foot pedal or button sends a signal to the control system. In response, the control system causes components within the surgical console to perform as described above to cause actuation of the piston.

At step 516, the control system causes the fluid source to inject fluid into the irrigation line. This causes pressure within the hydraulic chamber of the hand-piece. This pressure then moves the piston forward. Because the piston is physically connected with an IOL interface, which holds the IOL, the IOL moves forward along with the piston.

At step 514, the control system causes the aspiration pump to operate in reverse and pump fluid back into the aspiration line. This also creates pressure within the hydraulic chamber of the hand-piece. This pressure moves the piston forward in the distal direction. In some examples, step 516 is performed alone to actuate the piston. In some examples, step 514 is performed alone to actuate the piston. In some examples, both steps 514 and 516 are performed together to actuate the piston.

In some implementations, the control system can monitor the fluid that goes into and out of the hydraulic chamber 204. This can allow the control system to provide more precise control over the piston. For example, the control system may be provided with the dimensions of the hydraulic chamber 204. The control system may thus calculate the amount of fluid that will move the piston a specific distance. By monitoring the fluid pumped into or out of the hydraulic chamber 204, the control system can stop pumping to stop movement of the piston after it has moved a predetermined distance. Such distance may be controlled by a user through one of the input mechanisms described above.

In the example of using the foot pedal with the master chamber as a driving mechanism, step 512 includes the user engaging the foot pedal. As described above, this presses fluid out of a master chamber within the foot pedal and into a slave chamber within the hand-piece. This moves the piston forward in the distal direction.

Other driving mechanisms may be used to drive the hydraulically-driven IOL insertion tool. In one example, the hydraulically-driven IOL insertion tool may be driven by gas forced infusion. This involves injecting a gas into one of the fluid lines to pressurize fluid within the hydraulic chamber and move the piston forward in a distal direction.

Through use of principles described herein, IOL insertion can be done using a hydraulically-driven IOL insertion tool. The hydraulically-driven IOL insertion tool provides a smooth, controlled, forward movement of the IOL into the patient's eye that is difficult to achieve with a hand-powered IOL insertion tool. Additionally, the hand-piece may be designed to be a single-use device.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A hydraulically-driven Intra-Ocular Lens (IOL) insertion tool comprising:
    a body;
    a chamber within the body;
    a first fluid port providing fluid communication into the chamber;
    a piston positioned within the chamber and arranged to move within the chamber in a first direction in response to the introduction of fluid into the chamber, and in a second, opposite direction in response to the removal of fluid from the chamber; and
    an elongated member comprising:
        a distal end comprising an intra-ocular lens interface; and
        a proximal end connected to the piston such that movement of the piston within the chamber causes corresponding movement of the elongated member.

2. The hydraulically-driven IOL insertion tool of claim 1, wherein the first fluid port comprises a check valve that allows fluid to enter the chamber and prevents fluid from exiting the chamber.

3. The hydraulically-driven IOL insertion tool of claim 1, wherein the first fluid port is connected to an irrigation line.

4. The hydraulically-driven IOL insertion tool of claim 1, further comprising, a second fluid port providing fluid communication into and out of the chamber.

5. The hydraulically-driven IOL insertion tool of claim 4, wherein the second fluid port is connected to an aspiration line.

6. The hydraulically-driven IOL insertion tool of claim 1, further comprising a surgical console comprising:
    a fluid source in fluid communication with the chamber; and
    an aspiration pump in fluid communication with the chamber.

7. The hydraulically-driven IOL insertion tool of claim 1, further comprising a foot pedal that includes a master hydraulic chamber in fluid communication with the chamber, the chamber acting as a slave chamber.

8. A system for Intra-Ocular Lens (IOL) insertion, the system comprising:
    a surgical console comprising:
        a fluid source; and
        an aspiration pump;
    a hydraulically-driven IOL insertion tool comprising:
        a chamber;
        a first fluid port in fluid connection with the chamber;
        a second fluid port in fluid connection with the chamber;
        a piston in connection with an elongated member, the elongated member having a distal end comprising an intra-ocular lens interface;
        a first fluid line providing fluid communication between the fluid source and the first fluid port;
        a second fluid line providing fluid communication between the aspiration pump and the second fluid port;
    wherein the piston is positioned within the chamber and arranged to move within the chamber in a first direction in response to the introduction of fluid into the chamber, and in a second, opposite direction in response to the removal of fluid from the chamber.

9. The system of claim 8, wherein the aspiration pump is one of an elastomeric pump and a peristaltic pump.

10. The system of claim 8, wherein the surgical console further comprises a control system.

11. The system of claim 10, wherein the control system causes the piston to move by providing fluid from the fluid source through the first fluid line into the chamber.

12. The system of claim 10, wherein the aspiration pump is configured to be operated in a forward condition resulting in aspiration of fluid by the aspiration pump or a reverse condition resulting in pushing of fluid in a direction, and further wherein the control system causes the piston to move by operating the aspiration pump in a reverse condition to push fluid into the chamber.

13. The system of claim 10, wherein the aspiration pump is configured to be operated in a forward condition resulting in aspiration of fluid by the aspiration pump in a first direction or a reverse condition resulting in pushing of fluid in a second direction opposite the first direction, and further wherein the control system causes the piston to move by both providing fluid from the fluid source through the first fluid line into the chamber and operating the aspiration pump in a reverse condition to push fluid into the chamber.

14. The system of claim 10, wherein the control system causes the piston to move in response to a signal from a foot pedal connected to the surgical console.

15. The system of claim 10, wherein the fluid source is a saline fluid that is injectable into an eye during ophthalmic surgical procedures.

* * * * *